(12) United States Patent
Catbagan et al.

(10) Patent No.: US 7,670,360 B2
(45) Date of Patent: Mar. 2, 2010

(54) LOW PROFILE ANTERIOR THORACIC AND THORACOLUMBAR PLATE

(75) Inventors: Adrian Catbagan, Quezon (PH); Jude L. Sasing, Quezon (PH); Agustin G. Morales, Cebu (PH); Jose Martin S. Paiso, Las Pinas (PH); Edwin C. Madera, Caloocan (PH); Jeffrey B. Bajo, Makati (PH); Ramon B. Gustilo, Minneapolis, MN (US)

(73) Assignee: Orthopaedic International, Inc., Cabuyao, Laguna (PH)

( * ) Notice: Subject to any disclaimer, the term of this patent is extended or adjusted under 35 U.S.C. 154(b) by 753 days.

(21) Appl. No.: 10/904,912

(22) Filed: Dec. 3, 2004

(65) Prior Publication Data

US 2005/0288673 A1 Dec. 29, 2005

Related U.S. Application Data

(60) Provisional application No. 60/530,758, filed on Dec. 19, 2003.

(51) Int. Cl.
*A61B 17/80* (2006.01)
(52) U.S. Cl. .................... 606/280; 606/286
(58) Field of Classification Search ............ 606/69–71; 411/429, 533
See application file for complete search history.

(56) References Cited

U.S. PATENT DOCUMENTS

| | | | | |
|---|---|---|---|---|
| 4,696,290 A | * | 9/1987 | Steffee | 606/61 |
| 4,836,196 A | * | 6/1989 | Park et al. | 606/61 |
| 5,201,734 A | * | 4/1993 | Cozad et al. | 606/62 |
| 5,261,910 A | * | 11/1993 | Warden et al. | 606/61 |
| 5,324,290 A | | 6/1994 | Zdeblick et al. | |
| 5,393,182 A | * | 2/1995 | Berecz | 411/369 |
| 5,395,371 A | * | 3/1995 | Miller et al. | 606/61 |
| 5,527,314 A | | 6/1996 | Brumfield et al. | |
| 5,603,714 A | | 2/1997 | Kaneda et al. | |
| 5,716,355 A | | 2/1998 | Jackson et al. | |
| 8,208,882 | | 3/2001 | Cohen | |
| 6,244,807 B1 | * | 6/2001 | Garcia | 411/369 |
| 6,261,288 B1 | | 7/2001 | Jackson | |
| 6,315,779 B1 | * | 11/2001 | Morrison et al. | 606/281 |
| 6,342,055 B1 | | 1/2002 | Eisermann et al. | |
| 6,402,751 B1 | | 6/2002 | Hoeck et al. | |
| 6,755,833 B1 | | 6/2004 | Paul et al. | |
| 6,764,489 B2 | * | 7/2004 | Ferree | 606/61 |

\* cited by examiner

*Primary Examiner*—Thomas C Barrett
*Assistant Examiner*—Nicholas Woodall
(74) *Attorney, Agent, or Firm*—Kagan Binder, PLLC

(57) ABSTRACT

A spinal implant assembly is provided for stabilizing the spine. The assembly includes an elongated plate, bolts, and nuts. The plate is fixed to vertebrae spanning an injury or deformity to a disc or vertebra using the bolts and nuts. Screws can provide additional stability. The nuts are configured to extend through the plate to clamp the plate between collars on both the bolts and nuts.

20 Claims, 8 Drawing Sheets

LOW PROFILE ANTERIOR THORACIC AND THORACOLUMBAR PLATE

FIELD OF THE INVENTION

The present invention pertains to implantable devices for stabilizing the spine. In particular, the invention relates to a plate-based system for anterior internal fixation of the spine.

BACKGROUND OF THE INVENTION

The general use of either rods or plates fixed to the vertebrae above and below a defect such as a fracture, ruptured disc, tumor, or deformity, is known, especially in the thoracic and thoracolumbar spine. The system disclosed in U.S. Pat. No. 5,603,714 uses rods to connect screws threaded into each vertebra spanning the defect. The advantage of a rod-based system is its flexibility to accommodate different indications using the same basic components. A disadvantage of rod-based systems is in the distance the device extends outwardly from the vertebrae, potentially affecting the surrounding muscle and causing pain to the patient.

A plate-based system can have a lower profile than a rod-based system. The application technique for a plate-based system is generally more straightforward than a rod-based system. Most plate-based systems include a plate sized to span one or more disc spaces, and screws or bolts to fasten the plate to the vertebrae. Various plate-based systems are disclosed in U.S. Pat. Nos. 5,324,290, 6,206,882, 6,342,055, and 6,755,833.

SUMMARY OF THE INVENTION

The invention involves a bone fixation assembly including a plate, at least one bolt, and at least one nut. The plate has a slot extending along a portion of the plate length and at least one aperture, both configured to receive the bolt and nut. The bolt has a threaded lower region, a collar and a threaded head. The nut has a lower extended portion, a collar and an upper portion. The slot and aperture in the plate are sized to receive the lower extended portion of the nut. The nut can be internally threaded to mate with the threaded bolt head. In some embodiments, the upper portion of the nut has one or more flat sides.

In one embodiment of the invention, the edges of the slot and aperture are chamfered. The chamfers can be continuous or there can be a plurality of discrete chamfers. In some embodiments, both the top and bottom surfaces of the plate have chamfers surrounding the slot and aperture. In these embodiments, the chamfers on the bottom surface of the plate are configured to receive the bolt collar and the chamfers on the top surface of the plate are configured to receive the nut collar.

In another embodiment of the invention, the assembly also includes at least one screw and the plate has at least one screw hole. The screw hole can be positioned adjacent the slot along the width of the plate. Additional screw holes can be positioned adjacent the aperture and in a middle portion of the plate. The screw holes can be in the same side of the plate, opposite the slot and bolt aperture.

The invention also involves a method of internally stabilizing vertebrae spanning a defect or injury using a plate assembly including a plate, bolts, and nuts. The method includes the steps of threading the bolts into vertebrae spanning the defect or injury, placing the plate over the bolts such that the bolt collars contact the plate and the bolt heads extend through the slot and aperture, and threading the nuts onto the bolt heads such that the lower extended portions of the nuts extend through the slot and aperture and the nut collars contact the plate. The plate is thereby clamped to the bolts.

The method can also include threading one or more screws through screw holes in the plate and into the vertebrae. In a further embodiment, a graft is positioned at the site of the defect or injury, and one or more screws are threaded through screw hole in the plate and into the graft. Additionally, the method can include the step of sliding the plate relative to the bolt within the slot to achieve a desired degree of compression prior to tightening the nuts on the bolts.

DETAILED DESCRIPTION OF THE INVENTION

The current invention is a device for anterior fixation of the spine, particularly the thoracic and thoracolumbar regions. The device includes a plate and a pair of bolts with matching nuts. In some embodiments, the device also includes one or more screws. The device has a low profile due to the design of the nut and the corresponding slot and bolt aperture in the plate. The plate has a single-slot design that minimizes spreading of the slotted portion of the plate when the nut is tightened on the bolt, thereby reducing the stress on the plate. In some embodiments, the plate also incorporates a protrusion to accommodate a screw hole beside the slot while maintaining plate strength and keeping a narrow width in other portions of the plate.

Figure 1:
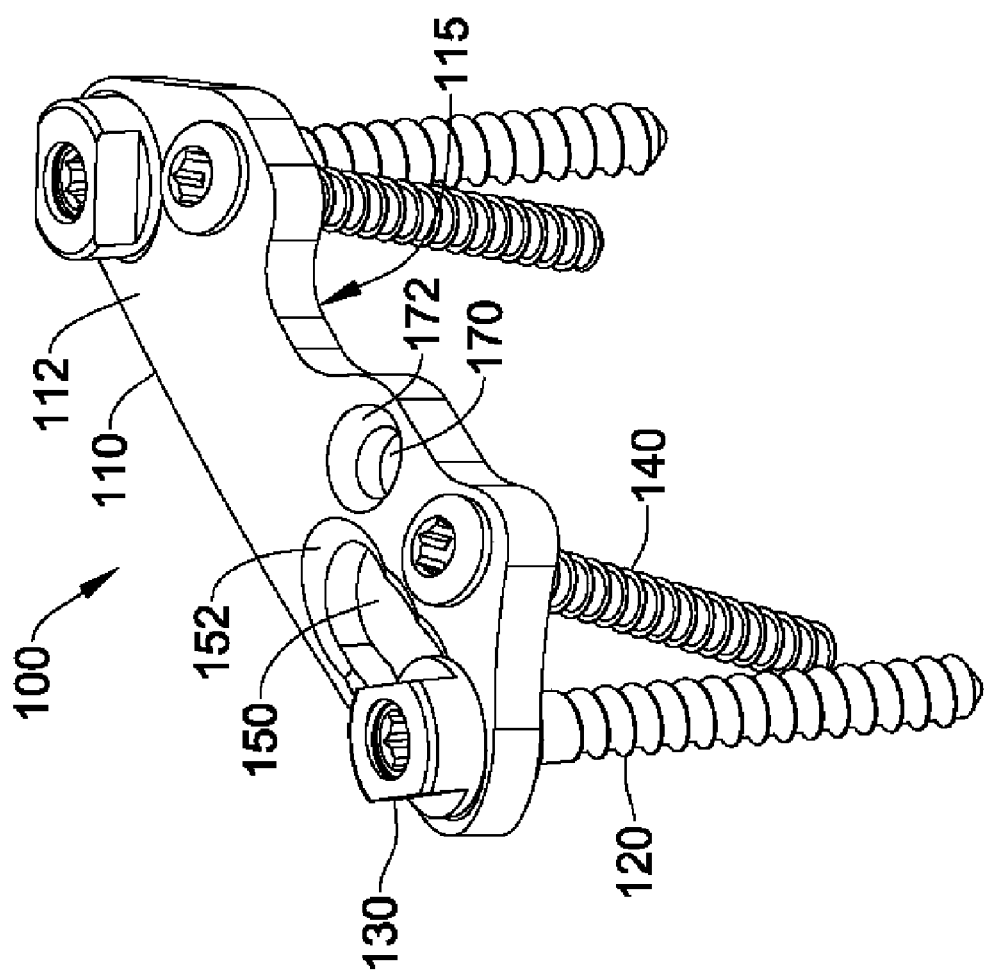
FIG. 1 is a perspective view of a plate assembly according to an embodiment of the invention.

Referring now to the drawings wherein like reference numerals refer to like elements throughout the several views, FIG. 1 shows a plate assembly 100 according to one embodiment of the invention. The assembly 100 includes an elongated plate 110, bolts 120, nuts 130, and screws 140. The elongated plate 110 is sized and configured to span a deformed or injured vertebrae or disc and to be fixed to the vertebrae above and below the deformity or injury.

Figure 2:
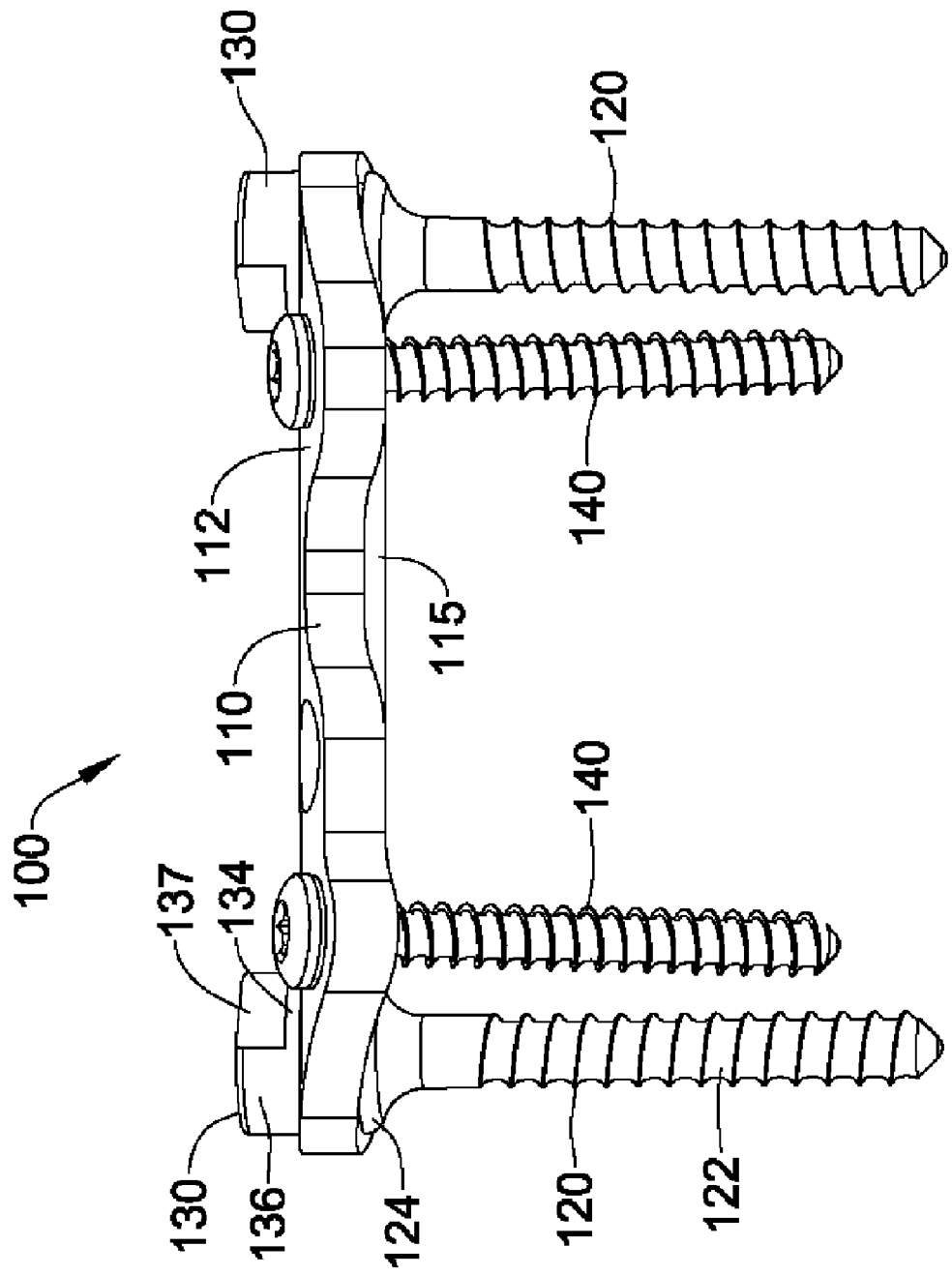
FIG. 2 is a side view of the plate assembly of FIG. 1.

The bolt 120 has a threaded body 122 that is threaded into the vertebrae, and a threaded head 126 that mates with a nut 130. The nut 130 clamps the plate 110 onto the bolt head 126. The overall profile of the assembly 100 is very low due to the design of the nut 130, bolt 120, and plate 110. See FIG. 2. The nut 130 has an extended lower region 132 that allows it to be embedded deeper into the plate 110, while maintaining adequate thread purchase on the threaded bolt head 126. The plate 110 has a slot 150 on one end that allows the bolt 120 to slide relative to the plate 110 in order to accommodate bone graft compression. The plate 110 also has an aperture 160 on the other end to accommodate another bolt 120. The slot 150 and aperture 160 can be on the same side of the plate. Screw holes 170, sized to receive screws 140, can be located on both ends of the plate 110 for added stability.

The embodiment shown in FIG. 1 includes a plate 110, two bolts 120, two nuts 130, and two screws 140. Those skilled in the art will recognize that whether or not screws are used will depend on the degree of fixation desired. Additionally, the number of screw holes 170 provided in the plate 110 and the number of screws 140 used in implanting the plate 110 can vary from as few as one to four or more depending on the degree to which the plate 110 is to be fixed to the vertebrae and whether or not it is desired to place one or more screws 140 into a graft between the vertebrae. The number of screws 140 utilized in implanting the plate 110 can also depend on the location of the plate 110 along the spine, the severity of the defect or injury, and the number of vertebrae to be stabilized.

Figure 3:
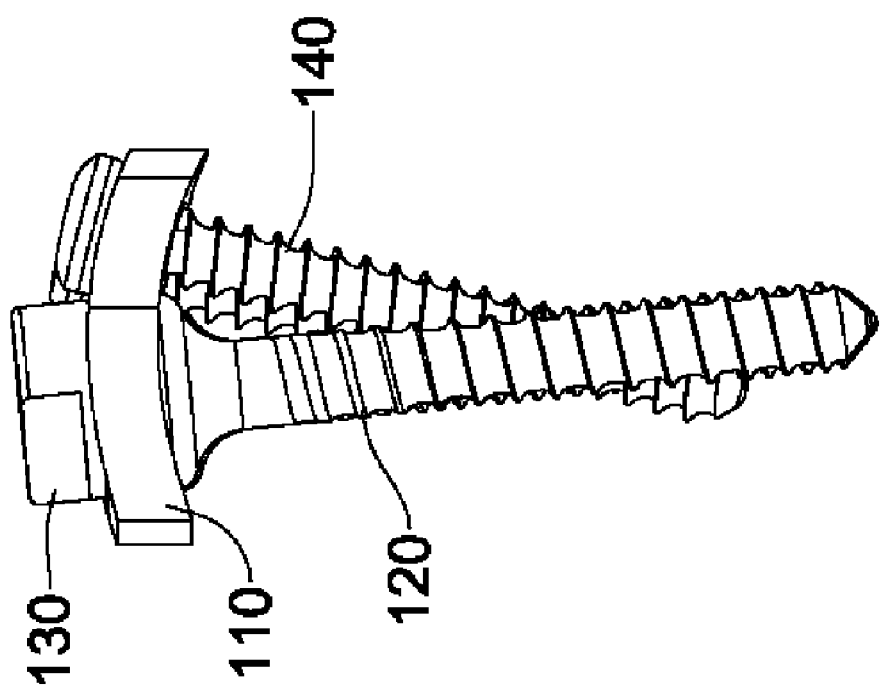
FIG. 3 is an end view of the plate assembly of FIG. 1.
Figure 5:
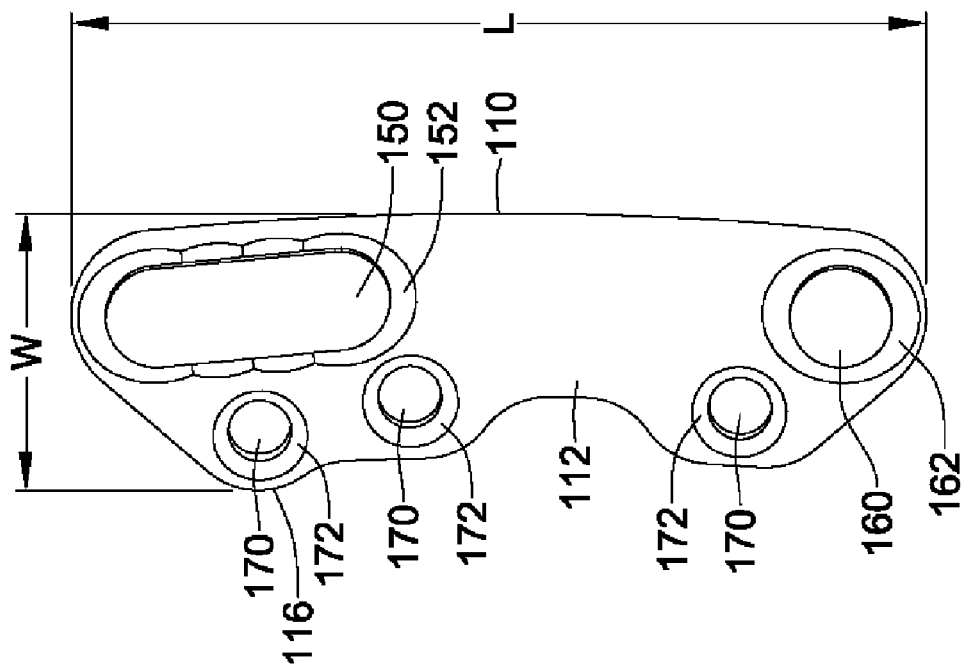
FIG. 5 is a top view of a plate according to an embodiment of the invention.

The plate 110 has a width W and length L as shown in FIG. 5. The plate 110 is curved across the width to match the curvature of the vertebral bodies. See FIG. 3. In one embodiment, the plate is substantially straight along the length. In another embodiment, the plate can have a kyphotic curve along the length when intended for the thoracic spine. Alternatively, plates with a lordotic curve can be used in the lumbar region. In a further embodiment, the plate can have a curve at only one end or may have multiple curves for use in a transition region, for example, between the thoracic and lumbar regions.

The plate has a slot 150 extending substantially longitudinally at one end, and an aperture 160 for a bolt 120 at the other end. The slot 150 and the aperture 160 are sized to accommodate the nut 130, which mates with the bolt 120. Screw holes 170 near the ends of the plate 110 allow fixation screws 140 to be inserted through the plate 110 and into the vertebral bodies. Screw holes 170 near the middle of the plate 110 allow fixation screws 140 to be inserted through the plate 110 and into a bone graft to stabilize the bone graft. In one embodiment, the slot 150 and aperture 160 are positioned toward one side of the plate 110 and the screw holes 170 are positioned toward the opposite side of the plate 110. See FIG. 5.

The screw holes 170 have chamfers 172 on the plate top 112 that allow the head 146 of the fixation screw 140 to be embedded into the plate 110, minimizing the exposed height of the screw head 146 above the vertebral body. The chamfers 172 around the screw holes 170 can be spherical, elliptical, or any other shape corresponding to the shape of the screw head 146.

The longitudinal slot 150 in the plate 110 allows the bolt 120 to slide relative to the plate 110 before it is fixed with the nut 130. This provides some length adjustability and allows for compression of the bone graft between the vertebral bodies. Top chamfers 152, 162 surrounding the slot 150 and aperture 160, respectively, on the plate top 112 ensure proper seating of the nut 130 on the plate 110 as well as reduce the overall height of the assembly 100 above the vertebral bodies.

Figure 4:
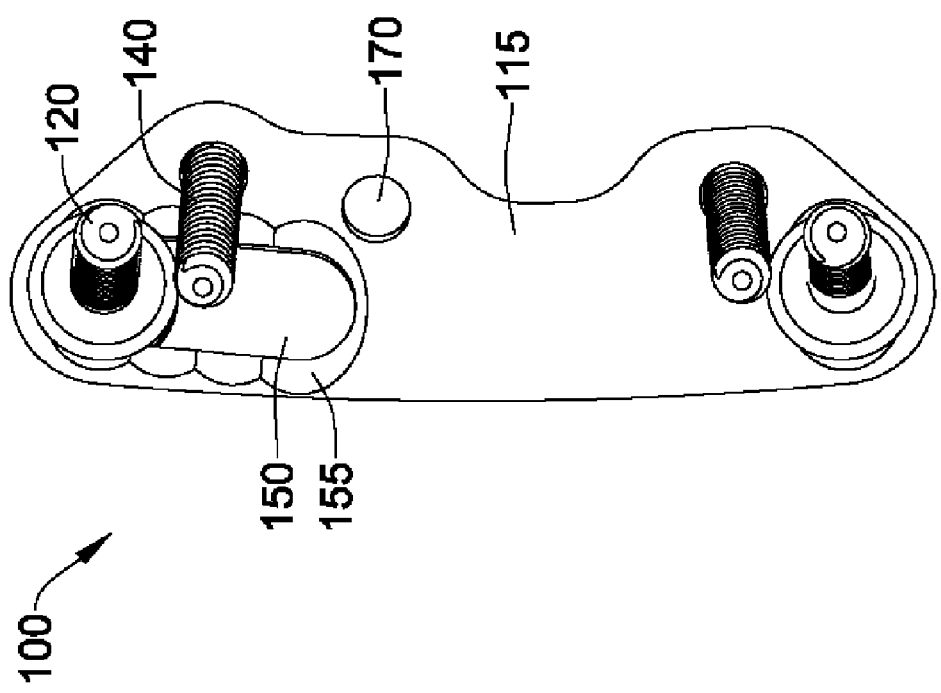
FIG. 4 is a bottom view of the plate assembly of FIG. 1.
Figure 6:
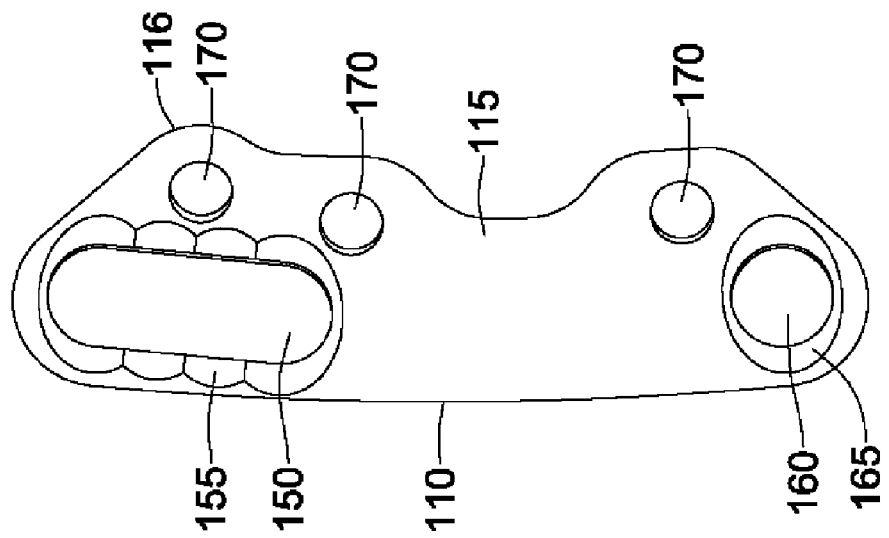
FIG. 6 is a bottom view of the plate of FIG. 5.

The bolt 120 has a threaded portion 122, which is threaded into the vertebral body, a collar 124 that abuts with the concave bottom 115 of the plate 110, and a threaded head 126 which mates with the nut 130. In one embodiment, the top and bottom chamfers 152, 155 surrounding the slot are discrete to provide definitive locations for the bolt collar 124 and nut collar 134 to be seated along the slot 150. See FIGS. 4-6. The bolt 120 has a socket 128 extending partially into the top of the head 126. The socket 128 is configured to engage a tightening device. In the embodiment shown in FIG. 7, the socket 128 has a hexagonal shape that engages a hexagonal driver. In another embodiment, the socket 128 can be square or any other shape to match a particular tightening device. The socket 128 is used for threading the bolt 120 into the vertebral body. The socket 128 is also used to prevent the bolt 120 from turning with the nut 130 when the nut 130 is tightened.

Figure 7:
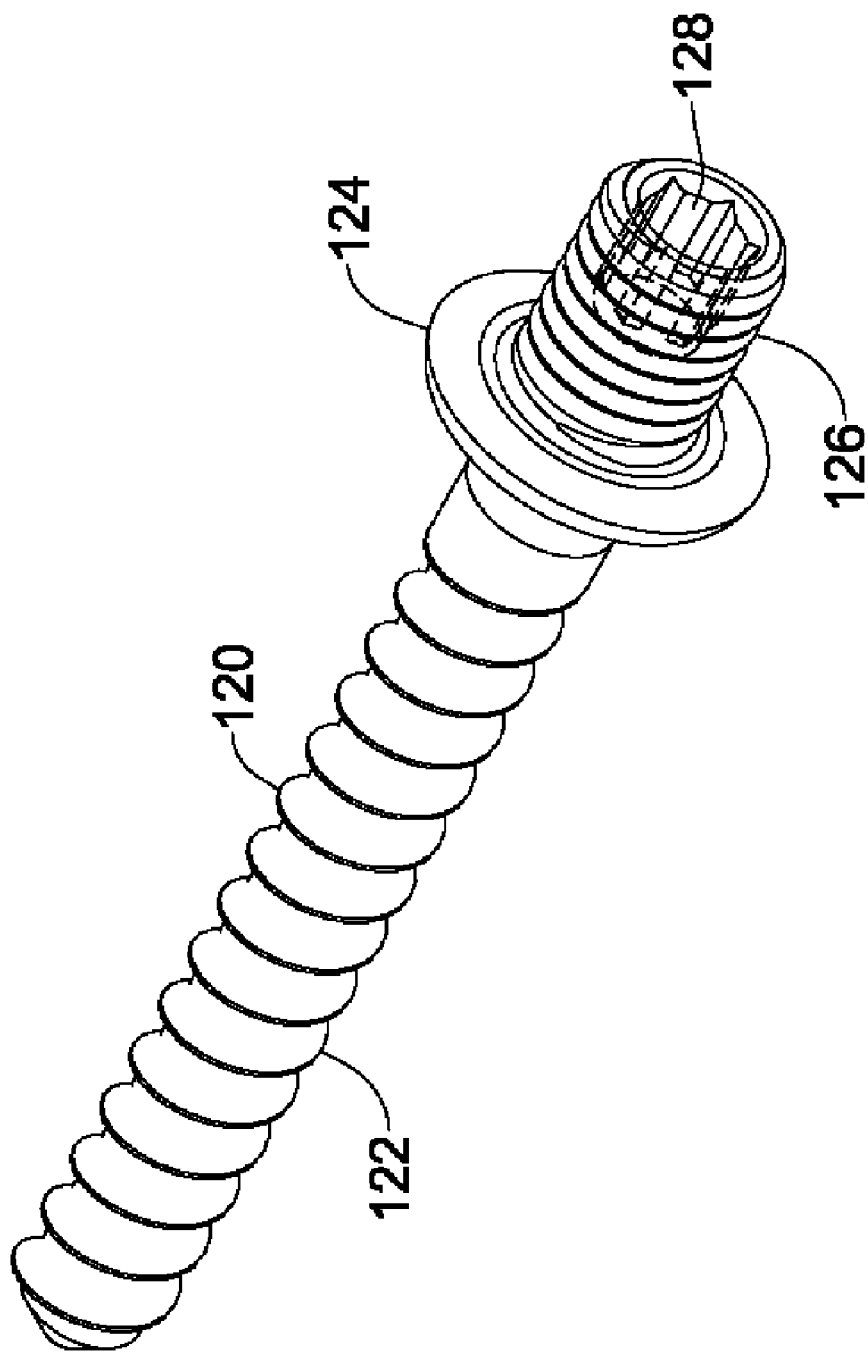
FIG. 7 is a perspective view of a bolt according to an embodiment of the invention.

As shown in FIG. 7, the internal socket 128 extends only partially into the end of the bolt 120, leaving the region adjacent the collar 124 with a full cross sectional area of the bolt 120. The cross sectional area is reduced in the region of the internal socket 128, causing the head 126 to be weaker in the region of the socket 128 than in the region adjacent the collar 124. The threaded head 126 of the bolt 120 at the level of the socket 128 is thus not used for clamping the plate 110 onto the bolt 120. Instead, the clamping force that clamps the plate 110 onto the bolt 120 comes from the threads below the level of the socket 128, adjacent the collar 124.

The plate bottom 115 has bottom chamfers 155, 165 surrounding the slot 150 and aperture 160, respectively. The bottom chamfers 155, 165 are configured to receive the bolt collar 124. The top and bottom chamfers 152, 155, 162, 165 are spherical, elliptical, or any other shape corresponding to the shape of the bolt collar 124 and nut collar 134. The top chamfers 152, 162 and bottom chamfers 155, 165 aid in aligning the bolt 120 within the slot 150 or aperture 160, and also serve to distribute the clamping force of the bolt 120 and nut 130 over a wider surface area on the plate 110. The chamfered design of the plate 110 also aids in reducing the height of the assembly 100 above the vertebral body surface while maintaining a secure clamping region for the bolts 120 and nuts 130.

Figure 10:
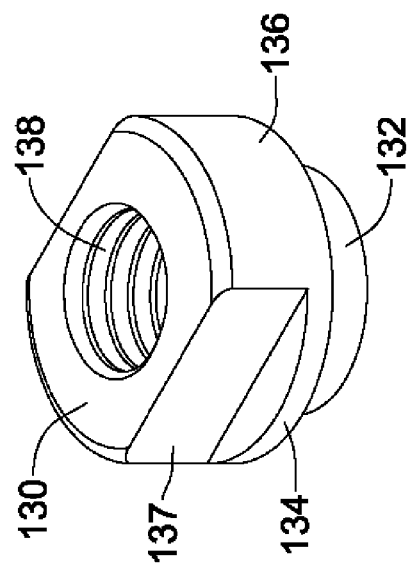
FIG. 10 is a top perspective view of the nut of FIG. 8.
Figure 9:
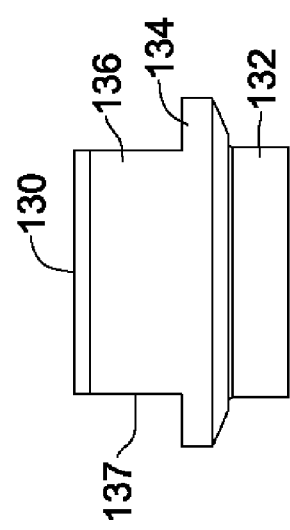
FIG. 9 is a side view of the nut of FIG. 8.
Figure 8:
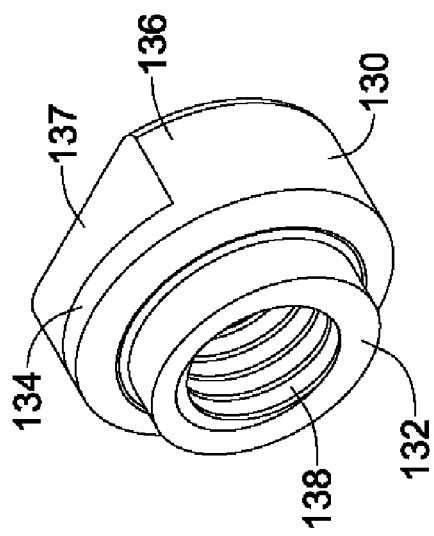
FIG. 8 is a bottom perspective view of a nut according to an embodiment of the invention.

As shown in FIGS. 8-10, the nut 130 has an extended lower portion 132 and a head portion 136. The head portion 136 has two or more flat sides 137 for engaging a tightening device such as a wrench. The flat sides 137 extend along the upper region of the head 136, leaving a collar 134 extending outward at the bottom of the head 136. The nut 130 has internal threads 138 throughout its length that mate with the threads on the bolt head 126.

After a plate 110 is placed over a bolt 120, a nut 130 is threaded over the bolt head 126 and the extended portion 132 of the nut 130 fits through the plate slot 150 or bolt aperture 160. When the nut 130 is tightened on the bolt head 126, the plate 110 is held between the nut collar 134 and the bolt collar 124. See FIG. 2. Although the level of the bolt socket 128 with its reduced cross section is within the nut 130, the clamping force on the plate 110 is not compromised because the extended cylindrical portion 132 of the nut 130 engages the threads on the bolt head 126 below the level of the socket 128. It is the extended portion 132 of the nut 130 that exerts the clamping force on the threaded bolt head region adjacent the bolt collar 124. The extended portion 132 allows the nut 130 to be embedded into the plate 110, thus minimizing the height of the construct above the vertebral body surface.

Figure 11:
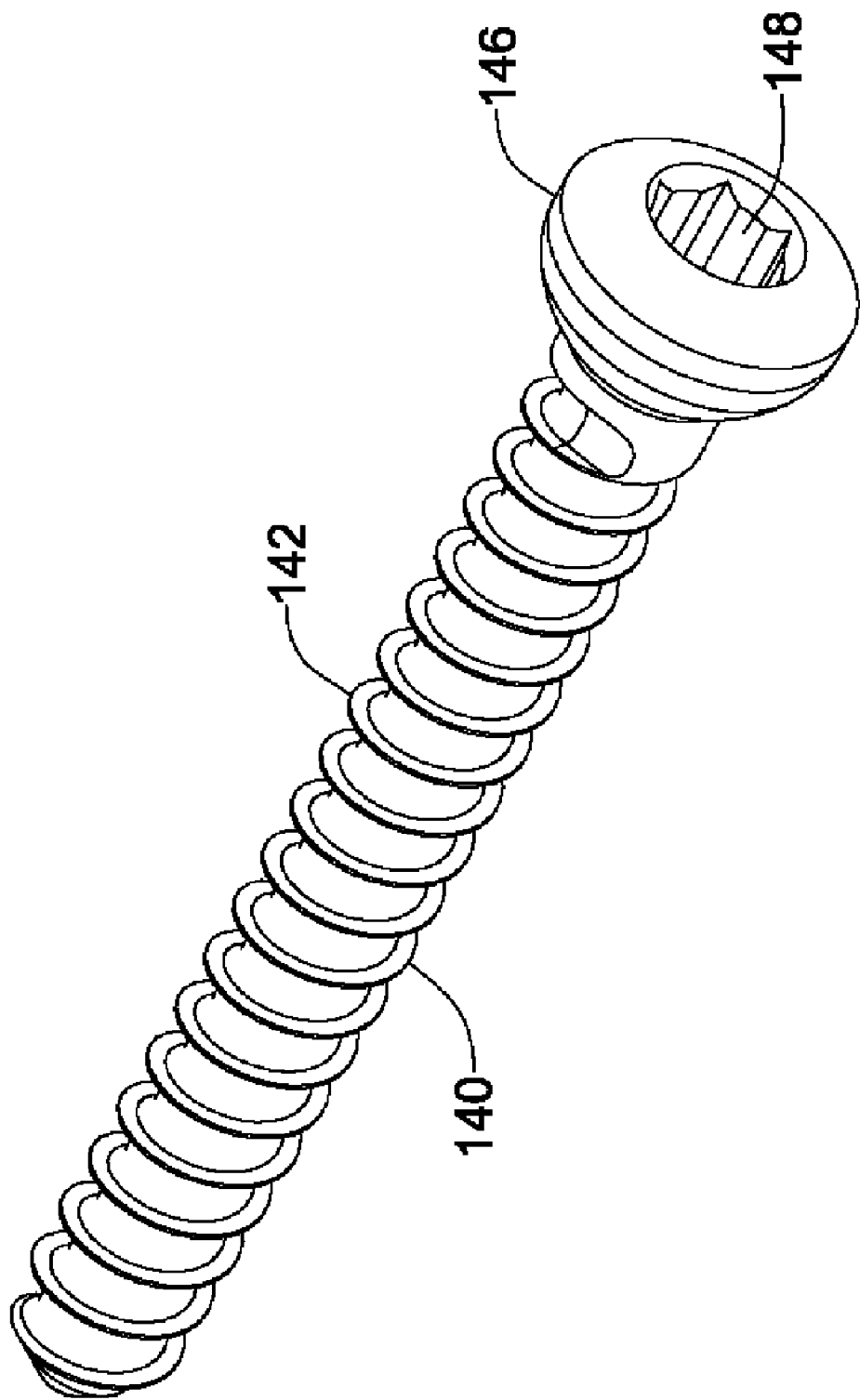
FIG. 11 is a perspective view of a screw according to an embodiment of the invention.

The screw 140 can be a conventional bone screw. In one embodiment, the screw 140 has a threaded body 142 and a head 146. The screw head 146 is seated in the screw hole chamfer 172 when the screw 140 is inserted through the plate 110. The screw head 146 is configured to mate with a tightening device. In the embodiment shown in FIG. 11, the screw head 146 has an internal hexagonal socket 148. In other embodiments, the screw head 146 can have any shape of internal socket, groove, depression, or protrusion that mates with a tightening device.

The plate 110 allows for a relatively wide slot 150 to accommodate the extended portion 132 of the nut 130. In order to accommodate a screw hole 170 beside the slot 150, while maintaining adequate plate strength, the plate 110 incorporates a protrusion 116 in its profile. This protrusion 116 maintains adequate plate strength while keeping the plate width narrow in all other portions of the plate 110. The screw hole 170 beside the slot 150 allows placement of a stabilizing screw 140 into the same vertebral body as the bolt 120 that is contained in the slot 150. In some embodiments a screw hole 170 is positioned adjacent the bolt aperture 160, allowing placement of a screw 140 into the same vertebral body as the bolt 120 contained in the aperture 160. See FIGS. 1 and 4. The spacing and orientation of the slot 150, aperture 160 and screw holes 170 can be selected to achieve a desired dynamic load sharing arrangement between the bolts 120 and screws 140.

In use, a bolt 120 is threaded into each of the vertebral bodies spanning a spinal defect or injury. The plate 110 is placed on top of the bolts 120 with the bolt heads 126 extending up through the slot 150 and aperture 160, and nuts 130 are threaded onto the bolt heads 126. In some embodiments, the injured or deformed disc and/or vertebra is replaced with a bone graft. Compression of the bone graft, if desired, is achieved by sliding the plate 110 relative to the bolt 120 within the slot 150. The bolt 120 in the slot 150 is positioned such that the bolt collar 124 is seated in one of the chamfers 155 on the bottom of the plate, and the nut collar 134 is seated in the corresponding chamfer 152 on the top of the plate. The nuts 130 are tightened to clamp the plate 110 onto the bolts 120. One or more screws 140 are then threaded into the vertebral bodies through the holes 170 in the plate 110. One or more additional screws 140 can be inserted through the remaining holes 170 into the graft for added stability. The screws 140 are tightened such that the screw heads 146 are seated in the chamfers 172 surrounding the holes 170.

The single-slot design of the plate minimizes spreading of the slotted portion when the nut is tightened on the bolt, thereby reducing the stress on the plate. The chamfered slot and bolt aperture and collars on both the bolt and nut provide a larger surface area for the clamping force while maintaining a low profile over the vertebrae. The plate has a screw hole beside the slot to allow both a bolt and screw to be inserted into the same vertebra. Additional screw holes allow for screws to be inserted into a graft.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A bone fixation assembly comprising:
    a plate having a length, a width, first and second sides, and first and second opposing edges across the width; the plate having a slot extending along a portion of the length and at least one aperture adjacent to the slot;
    at least one bolt comprising:
        a bolt collar having first and second opposite planar surfaces;
        a lower portion extending from the first planar surface of the bolt collar and having an outer threaded surface; and
        a head portion extending from the second planar surface of the bolt collar and having an outer threaded surface;
        wherein the head portion is extendible through one of the slot and aperture so that the second planar surface of the bolt collar is in contact with the first side of the plate; and
    at least one nut comprising:
        a first end and an opposite second end;
        a nut collar having first and second opposite surfaces;
        a lower extended portion extending from the first surface of the nut collar to the first end of the nut;
        an upper portion extending from the second surface of the nut collar to the second end of the nut; and
        an inner threaded surface extending through the upper portion, nut collar, and lower extended portion of the nut from the first end to the second end of the nut;
        wherein the nut comprises an integral structure made of a single material;
    wherein the inner threaded surface of the nut is threadingly engageable with the outer threaded surface of the head portion of the bolt so that the first surface of the nut collar is in contact with the second side of the plate.

2. The bone fixation assembly of claim 1, wherein the lower extended portion of the nut is positioned at least partially within the plate between its first and second sides.

3. The bone fixation assembly of claim 1, wherein the upper portion of the nut has one or more flat sides.

4. The bone fixation assembly of claim 1, wherein the slot and aperture are sized to receive the lower extended portion of the nut.

5. The bone fixation assembly of claim 1, wherein edges of the slot and aperture are chamfered.

6. The bone fixation assembly of claim 1, wherein edges of the slot and aperture have a plurality of discrete chamfers.

7. The bone fixation assembly of claim 1, wherein edges of the slot and aperture are chamfered on both the first side and the second side of the plate.

8. The bone fixation assembly of claim 7, wherein the chamfers on the second side of the plate are configured to receive the bolt collar and the chamfers on the first side of the plate are configured to receive the nut collar.

9. The bone fixation assembly of claim 1, wherein the slot and aperture are in opposite ends of the plate.

10. The bone fixation assembly of claim 1, further including at least one screw, wherein the plate has at least one screw hole configured for receiving the screw.

11. The bone fixation assembly of claim 10, wherein a screw hole is positioned adjacent the slot along the width of the plate.

12. The bone fixation assembly of claim 10, wherein the plate has two or more screw holes, wherein a first screw hole is adjacent a side of the slot and a second screw hole is adjacent the aperture.

13. The bone fixation assembly of claim 12, further comprising a third screw hole between the first and second screw holes.

14. The bone fixation assembly of claim 13, wherein the first, second, and third screw holes are in the same side of the plate.

15. An anterior spinal stabilization device comprising:
    an elongated plate having at least one slot and at least one aperture;
    a pair of bolts, each having a threaded body a bolt collar having opposite planar surfaces, and a threaded head; and
    a pair of nuts, each having a first end and a second end, a nut collar, an extended lower region extending from the nut collar to the first end of the nut, a head region extending from the nut collar to the second end of the nut and an internal threaded surface extending through the extended lower region, collar, and head region from the first end to the second end of the nut for threaded engagement with the threading on the bolt head, wherein the nut comprises an integral structure made of a single material;

wherein the plate, bolts, and nuts are configured such that when the bolt head extends through the slot or aperture, one of the planar surfaces of the bolt collar contacts a bottom surface of the plate and when the nut is threaded onto the bolt head, the extended lower region of the nut fits through the slot or aperture, and the nut collar contacts a top surface of the plate.

16. The anterior spinal stabilization device of claim 15, further comprising chamfers surrounding the slot and aperture.

17. The anterior spinal stabilization device of claim 15, further comprising chamfers surrounding the slot and aperture on both the bottom and top surfaces of the plate.

18. The anterior spinal stabilization device of claim 15, further comprising one or more screws.

19. The anterior spinal stabilization device of claim 18, wherein the plate has an aperture sized to receive a screw adjacent the slot across a width of the plate.

20. The anterior spinal stabilization device of claim 18, further comprising one or more apertures in a middle section of the plate sized to receive screws.

* * * * *

UNITED STATES PATENT AND TRADEMARK OFFICE
CERTIFICATE OF CORRECTION

PATENT NO. : 7,670,360 B2  Page 1 of 1
APPLICATION NO. : 10/904912
DATED : March 2, 2010
INVENTOR(S) : Adrian Catbagan et al.

It is certified that error appears in the above-identified patent and that said Letters Patent is hereby corrected as shown below:

On the title page, item [56],
U.S. PATENT DOCUMENTS, please delete "8,208,882" and insert in place thereof --6,206,882--.

Signed and Sealed this

Eighth Day of June, 2010

David J. Kappos
*Director of the United States Patent and Trademark Office*